United States Patent [19]

Jäger

[11] 3,979,469
[45] Sept. 7, 1976

[54] POLYFLUOROALKYL IODIDES, PROCESS FOR THEIR MANUFACTURE, AND THEIR USE

[75] Inventor: Horst Jäger, Bettingen, Switzerland

[73] Assignee: Ciba-Geigy Corporation, Ardsley, N.Y.

[22] Filed: Dec. 14, 1973

[21] Appl. No.: 425,011

[30] Foreign Application Priority Data

Dec. 21, 1972 Switzerland.................... 18662/72
Feb. 23, 1973 Switzerland........................ 2653/73

[52] U.S. Cl............................. 260/653; 260/488 B; 260/488 CD; 260/469; 260/48 T; 260/515 A; 260/539 R; 260/618 D; 260/632 R; 260/648 F; 260/651 F

[51] Int. Cl.².................. C07C 19/08; C07C 25/14

[58] Field of Search ....... 260/653.1 T, 653, 653.1 R

[56] References Cited
UNITED STATES PATENTS

| | | | |
|---|---|---|---|
| 2,972,638 | 2/1961 | Tiers ........................... | 260/653.1 T |
| 2,975,220 | 3/1961 | Hauptschein et al. ....... | 260/653.1 T |
| 3,454,657 | 7/1969 | Decker et al................ | 260/653.1 T |

FOREIGN PATENTS OR APPLICATIONS

| 1,319,898 | 6/1973 | United Kingdom .......... | 260/653.1 T |

Primary Examiner—D. Horwitz
Attorney, Agent, or Firm—Joseph G. Kolodny; Edward McC. Roberts; Prabodh I. Almaula

[57] ABSTRACT

New polyfluoroalkyl iodides of the formula

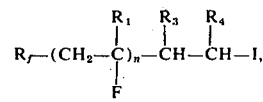

are provided, wherein $R_f$ represents a fluorinated hydrocarbon radical with 3 to 18 carbon atoms, $R_1$ represents hydrogen or fluorine, $R_3$ and $R_4$ each independently represents hydrogen, lower alkyl, hydroxyalkyl, carboxy, carbalkoxy, $-(CH_2)_pOCOR_2$, in which $R_2$ represents hydrogen or alkyl with 1 to 3 carbon atoms and p is 0 or a whole number from 1 to 3, phenyl and alkylphenyl, or $R_3$ and $R_4$ together with the carbon atoms to which they are bonded represent an optionally substituted cycloaliphatic radical with 5 or 6 ring carbon atoms, and $n$ is a whole number from 1 to 3.

The new compounds are useful as intermediates for the manufacture of oil- and water-repellents, as oil- and water-repellents per se, as lubricants and as surface active assistants.

8 Claims, No Drawings

POLYFLUOROALKYL IODIDES, PROCESS FOR THEIR MANUFACTURE, AND THEIR USE

It is known to react perfluoroalkyl iodides in the presence of suitable catalysts with olefines, e.g. ethylene, or halogenated olefines, e.g. vinyl fluoride or vinylidene fluoride, according to the following reaction equations:

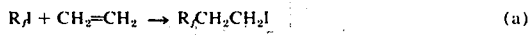  (a)

  (b)

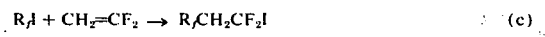  (c)

to yield in the main the perfluoroalkyl iodide-olefine 1,1-adducts in addition to higher telomers.

The present invention is based on the observation that it is possible to obtain valuable new compounds by the repeated addition of olefines to the iodides of the type (b) or (c). Whereas the addition to the perfluoroalkyl iodides of type (a) is not successful, the iodides of the formulae $R_fCH_2CHFI$ and $R_fCH_2CF_2I$ surprisingly are able to combine in good yield with ethylene and other olefines. The present invention therefore provides new polyfluoroalkyl iodides of the formula

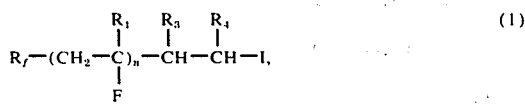  (1)

wherein $R_f$ represents a fluorinated hydrocarbon radical with 3 to 18 carbon atoms, $R_1$ represents hydrogen or fluorine, $R_3$ and $R_4$ each independently represents hydrogen, alkyl with 1 to 4 carbon atoms, hydroxyalkyl with 1 to 5 carbon atoms, carboxy, carbalkoxy with 1 to 4 carbon atoms in the alkyloxy moiety, $-(CH_2)_p$ $OCOR_2$, in which $R_2$ represents hydrogen or alkyl with 1 to 3 carbon atoms and $p$ is 0 or a whole number from 1 to 3, phenyl and alkylphenyl with 1 to 3 carbon atoms in the alkyl moiety, or $R_3$ and $R_4$ together with the carbon atoms to which they are bonded represent an optionally substituted cycloaliphatic radical with 5 or 6 ring carbon atoms, and $n$ is a whole number from 1 to 3.

The substituents $R_3$ and $R_4$ are each independently hydrogen, alkyl with 1 to 4 carbon atoms, methyl, ethyl, propyl, isopropyl, butyl, hydroxyalkyl with 1 to 5 carbon atoms, e.g. hydroxymethyl, hydroxyethyl, hydroxypropyl, hydroxybutyl, and hydroxyamyl, the radicals $-COOH$, $-COOR$, and $-OOCR$ in which R represents methyl, ethyl, propyl and butyl, and $-(CH_2)_pOOCR_2$, wherein $R_2$ represents hydrogen, methyl, ethyl, propyl, or isopropyl, and $p$ is 0 or a whole number from 1 to 3, and are also phenyl, methyl, ethyl, or propylphenyl. Furthermore, the substituents $R_3$ and $R_4$, together with the carbon atoms to which they are bonded, represent a cyclopentyl or cyclohexyl ring which can contain the substituents $-(CH_2)_qOH$ and $(CH_2)_qOCOCH_3$; $q$ is a whole number from 1 to 3. Examples of further substituents are the radicals $-COOR'$, wherein $R'$ can be methyl or ethyl.

Preferred polyfluoroalkyl iodides are those in which one of the substituents $R_3$ or $R_4$ represents hydrogen and the other also represents hydrogen, methyl, or hydroxymethyl.

The perfluorinated hydrocarbon radical can be a branched or preferably a straight-chain perfluoroalkyl radical with 3 to 18 carbon atoms and is represented by the following formulae:

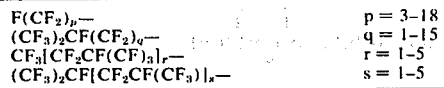

| | |
|---|---|
| $F(CF_2)_p-$ | $p = 3-18$ |
| $(CF_3)_2CF(CF_2)_q-$ | $q = 1-15$ |
| $CF_3[CF_2CF(CF_3)]_r-$ | $r = 1-5$ |
| $(CF_3)_2CF[CF_2CF(CF_3)]_s-$ | $s = 1-5$ |

Particularly interesting polyfluoroalkyl are those of the formula

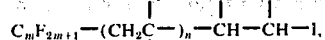  (2)

wherein $R_1$ represents hydrogen or fluorine, $R_5$ and $R_6$ each independently represents hydrogen, methyl, ethyl, hydroxymethyl, hydroxyethyl, carboxy, carbomethoxy, carboethoxy, $-OOCCH_3$, $-OOCC_2H_5$, $-CH_2OOCH$, $-CH_2OOCCH_3$, $-CH_2OOCC_2H_5$, phenyl, methylphenyl, or $R_5$ and $R_6$, together with the carbon atoms to which they are bonded, represent the radical of the formulae

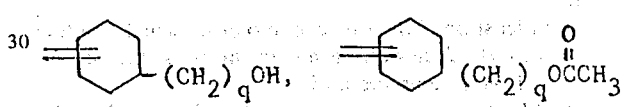

wherein $q$ is a whole number from 1 to 3 and $R'$ represents alkyl with 1 to 2 carbon atoms, $m$ is a whole number from 4 to 12, and $n$ is a whole number from 1 to 3.

Particularly suitable compounds are also those of the formula

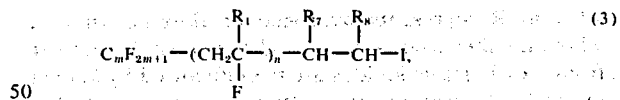  (3)

wherein $R_1$ represents hydrogen or fluorine, $R_7$ represents hydrogen, $R_8$ represents hydrogen, methyl, ethyl, hydroxymethyl, carboxy, carbomethoxy, carboethoxy, $-OOCCH_3$, $-CH_2OOCH$, $-CH_2OOCCH_3$, $-CH_2OOCC_2H_5$, phenyl, methylphenyl, or $R_7$ and $R_8$, together with the carbon atoms to which they are bonded, represent the radical of the formulae

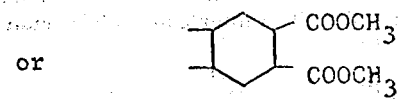

$m$ is a whole number from 4 to 12 and $n$ is a whole number from 1 to 3, and also of the formulae

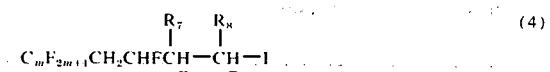 (4)

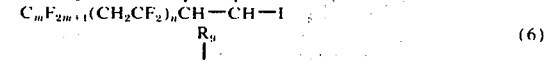 (5)

 (6)

(7)

wherein $R_7$, $R_8$, $m$ and $n$ have the indicated meanings, and $R_9$ represents hydrogen, methyl, or hydroxymethyl.

The invention also provides a process for the manufacture of the perfluoroalkyl iodides of the formula (1). The process consists in reacting a. compounds of the formula

 (8)

with b. at least one linear or cyclic olefine which contains at most 12 carbon atoms, in the presence of
c. at least one amine and
d. at least one metal salt of a metal of groups Ia to IVa or Ib to VIIb and VIII of the Periodic System, optionally in the form of an amine-metal complex, at 0°C to 350°C and 1 to 200 kp/cm².

In formula (8), the symbols $R_f$, $R_1$ and $n$ have the meaning given in formula (1).

As components (a) there are used preferably iodides of the formula

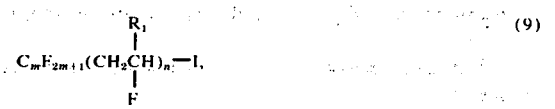 (9)

wherein R represents hydrogen or fluorine, $m$ is a whole number from 4 to 12 and $n$ is a whole number from 1 to 3. These iodides are manufactured by known methods. As component (b) there are used preferably linear or cyclic olefines with a maximum of 12 carbon atoms which have the formula

 (10)

wherein $R_3$ and $R_4$ have the meanings given for the formula (1). The olefines of component (b) are preferably alkenes or alkenes substituted with functional groups.

Suitable alkenes herein are in particular ethylene and propylene, and also butylene. Examples of alkenes which are substituted by functional groups are allyl alcohol, vinyl acetate, esters, e.g. lower alkyl esters of acrylic, methacrylic, crotonic, maleic, fumaric or itaconic acid, in particular allyl formiate and allyl acetate.

Cyclic olefines of particular interest have e.g. the formulae

(11) 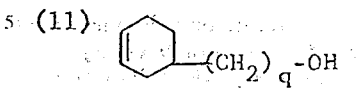

(12) 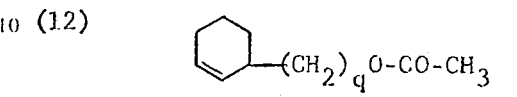

or

(13) 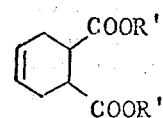

wherein $q$ is a whole number from 1 to 3 and $R'$ represents alkyl with 1 or 2 carbon atoms.

The olefines which are preferably used according to the invention therefore have the formulae

 (14),

 (15)

and

 (16), wherein $R_5$, $R_6$, $R_7$, $R_8$ and $R_9$ have the meanings given in the formulae (2), (3) and (6).

The adducts obtained according to the invention are often isomeric mixtures in that the polyfluoroalkyl radical can add on to both the α- and β-carbon atom of the ethylenically unsaturated bond of the olefine. In order to simplify matters, in general only the one isomeric form is specified herein.

The amines which are possible as component (c) are in particular primary, secondary, or tertiary aliphatic, heterocyclic, or aromatic amines. Preferred amines are those which contain at least one oxygen atom in the molecule. Particularly suitable amines in this connexion are those with one hydroxy group in the molecule. Especial interest attaches to amines which are able to form an amphoteric configuration, e.g. alkanolamines. Such alkanolamines contain preferably 2 to 6 carbon atoms.

The following amines may be cited: N-ethylethanolamine, aminoethylisopropanolamine, diethylethanolamine, n-(2-hydroxyethyl)-ethylenediamine, isopropanolamine; in particular diethanolamine, triethanolamine, and, preferably, monoethanolamine. Amines such as N-hydroxyethylmorpholine, morpholine, N-hydroxyethylpiperazine, 3-diethylamino-phenol, glycine, or diethylamine, are also suitable.

Suitable metal salts to be used according to the invention as component (d) are chiefly metal salts of a metal of groups Ib to VIIb and VIII, particularly of the 4th. to 6th. Period, of the Periodic System. Particularly suitable metal salts of metals of groups Ib and IIb in this connexion are e.g. copper-I, silver, gold, zinc, cadmium or mercury salts. Other preferred metal salts are derived from metals of groups IIIb or VIII, in particular of the 4th. or 5th. Period, or from metals of groups IVb or Vb, in particular of the 4th. to 6th. Period, of the Periodic System. The metal salts in question are yttrium, titanium, zirconium, niobium, tantalum, manganese, iron, ruthenium, or rhodium salts.

Suitable representatives of group Ia are e.g. sodium and potassium, and of group IIa e.g. magnesium, calcium, strontium, or barium. To the metals of group IIIa belong gallium, thallium, and indium, and to those of group IVa germanium, tin, or lead.

All references herein to the Periodic System are based on the Periodic System according to "Lange's Handbook of Chemistry", 10th. Edition, 1967, pp. 60 and 61.

The halides, e.g. the bromides, iodides, or, preferably, the chlorides, of the respective metals have proved particularly advantageous. But in addition it is also possible to use corresponding phosphates, carbonates, nitrates, sulphates, cyanides, hydrides, acetylacetonates, or alcoholates, e.g. ethylates or methylates. Mixtures of salts can be used as well, also of metals of different valency. Copper-I-chloride has proved particularly suitable.

Preferably, the components (c) and (d) are used as amine-metal salt complexes to which it is possible to add an excess of the complex-forming amine as solvent. Moreover, it is also possible for the amine-metal salt complex to contain an excess of unreacted metal salt.

The isolation and reuse of the amine-metal salt complex can be made easier by also using binding and adsorption agents as carrier for the catalyst complex. Suitable for this purpose are e.g. aluminium oxide, silicon dioxide, carbon, diatomaceous earth, or natural and synthetic molecular sieves.

The reaction of components (a) and (b) takes place preferably at 60°C to 250°C, ar especially at 120°C to 180°C.

Depending on whether the boiling points of components (a), (b) and (c) are below or above 60°C, the reaction is advantageously carried out in an autoclave or in a pressure-free apparatus at atmospheric pressure. A pressure is thereby created which depends on the amount of the components (a) and (b) introduced. The pressures are in the range from 1–200 kp/cm², preferably from 1–160 kp/cm², depending on the reactants. The reaction can be carried out continuously or batchwise.

The quantitative ratios between components (a), (b), (c) and (d) vary within fairly wide limits depending on how reactive the individual components are and what properties the end products are to have. The preferred procedure to be followed is that 1 mol of component (a) is reacted with 1 to 10 mols of component (b), in the presence of 0.05 to 10 mols of component (c) and 0.003 to 20 mols of component (d).

The reaction can be carried out in the absence or in the presence of a solvent. Examples of suitable solvents are fluorinated alkanes, fluorinated haloalkanes, alcohols, ethers, aromatic hydrocarbons, or cycloaliphatic compounds.

The new polyfluoroalkyl iodides are valuable intermediates which can be used for the synthesis of application products, e.g. for oil and water repellants. Moreover, they can also be used themselves as oil and water repellants for porous and non-porous substrates.

Perfluoroalkyl alkenes and perfluoroalkanes are obtained from the iodides by splitting off iodine by hydrogenation or by splitting off hydrogen iodide. The perfluoroalkyl alkenes can be converted into alkanes by subsequent hydrogenation.

In some cases, the splitting off of hydrogen iodide occurs during the reaction of the perfluoroalkyl iodides with the olefine. The resulting products then contain a double bond.

The functional groups present in the perfluoroalkyl iodides, e.g. hydroxy, carboxy, and ester groups, offer further reaction possibilities for the manufacture of secondary products. Thus, for example, esterification of the hydroxy group with acrylic, methacrylic, crotonic, itaconic, fumaric or maleic acid or e.g. allyl isocyanate yields reactive esters or carbamates which can be polymerised.

Reaction of an amino group with an acid chloride of the above cited acids yields a reactive amide which can be polymerised.

Carboxy groups can be esterified; the resulting esters, provided they are derived from unsaturated compounds, can also be polymerised, e.g. vinyl ester.

The application products manufactured from the intermediates described hereinabove are very suitable for finishing porous substrates (especially for rendering them oil and water repellent), e.g. textiles, paper, leather and wood, and also non-porous substrates, e.g. metal, glass or plastic surfaces.

It is also possible to use the compounds according to the invention direct as lubricants and as additives for hydraulic liquids, polishes and waxes, or also as surface-active assistants.

The following Examples illustrate the invention but do not limit it in any way. Parts and percentages are by weight unless otherwise stated.

EXAMPLE 1 a. 115 g (0,28 mol) of the compound of the formula

$C_4F_9CH_2CF_2I$ are put into an autoclave together with a catalyst consisting of 0.5 g of Cu Cl, 1.5 g of $Al_2O_3$ and 1.0 g of ethanolamine. The autoclave is sealed and cooled to −70°C, evacuated, sparged twice with nitrogen, and finally 20 g (0.71 mol) of ethylene are passed in under pressure. The reaction begins at 100°C and 22 kp/cm². The autoclave is kept for 6 hours at 150°C and 25 kp/cm² and then degassed. Yield: 58 g (40.70 of theory) of the compound of the formula

$C_4F_9CH_2CF_2CH_2CH_2I$

Boiling point: 186°–187,5°C.

The mass spectrum confirms this structure; the molecular weight found is 438 (calculated: 438). 60 g of the starting compound of the formula

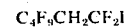

$C_4F_9CH_2CF_2I$ (b.p. 126°-127°C)

are recovered and can be used in a further reaction. (b) The following components are reacted as described in Example 1: 420 g of $C_4F_9CH_2CF_2I$, 50 g of ethylene, 10 g of catalyst consisting of 0.5 g of CuCl, 0.5 g of $SnCl_4$, 1.5 g of ethanolamine, 7.5 g of aluminium oxide as carrier. Reaction conditions: 7 hours at 140°C/26 kp/cm².
Yield: 442 g (98.5% of theory)
Boiling point: 99°–115°C/5 Torr
Mass spectrum M = 438, M − F = 419, M − I = 311
Analysis in gas chromatography: 95.6% $C_4F_9CH_2CF_2CH_2CH_2I$ remainder to 100% impurities.
The following catalysts can also be used instead of the cited ones: AuCN, CdSO₄, YCl₃, TiCl₄, Nb(OCH₃)₅, RuCl₃, RhCl₃, FeCl₃, KCN, GaCl₃, rhodium acetylacetonate.

EXAMPLE 2

28.8 g of $CF_3(CF_2)_n(CH_2CF_2)_oI$ (wherein $n = 5, 7, 9$ and $o = 1, 2$), 0.5 g of CuCl, 1.0 g of Al₂O₃, 0.5 g of ethanolamine, and 8 g of ethylene are reacted as described in Example 1.
Reaction conditions: 6 hours at 140°C; 24 kp/cm².
After gas chromatography and mass spectrum the yield is as follows:

| | | |
|---|---|---|
| 4.80 % of | starting material | |
| 4.00 % of | $C_6F_{13}CH_2CF_2CH_2CH_2I$ | M 538 |
| 59.5 % of | $C_8F_{17}CH_2CF_2CH_2CH_2I$ | M 638 |
| 23.50 % of | $C_{10}F_{21}CH_2CF_2CH_2CH_2I$ | M 738 |
| 5.23 % of | $C_6F_{13}(CH_2CF_2)_2CH_2CH_2I$ | M 602 | and a small residue of impurities.
Yield: 29.0 g (~100% of theory).

EXAMPLE 3

78 g of $CF_3(CF_2)_n(CH_2CF_2)_oI$ (wherein $n = 5, 7, 9$ and $o = 1, 2, 3$), 0.5 g of Cu Cl, 0.5 g of ethanolamine, 1.0 g of Al₂O₃, and 7.0 g of ethylene are reacted as described in Example 1.
Reaction conditions: 6 hours at 130°C; 18 kp/cm².
Reaction product: Composition according to gas chromatography: Mass spectrum

| | | |
|---|---|---|
| 25.50 % of | $C_{10}F_{21}CH_2CF_2CH_2CH_2I$ | M 738 |
| 11.76 % of | $C_6F_{13}(CH_2CF_2)_2CH_2CH_2I$ | M 602 |
| 23.42 % of | $C_8F_{17}(CH_2CF_2)_2CH_2CH_2I$ | M 702 |
| 26.00 % of | $C_{10}F_{21}(CH_2CF_2)_2CH_2CH_2I$ | M 802 |
| 3.10 % of | $C_6F_{13}(CH_2CF_2)_3CH_2CH_2I$ | M 666 |
| 1.82 % of | $C_8F_{17}(CH_2CF_2)_3CH_2CH_2I$ | M 766 |

Residue of starting material and impurities: < 1%.
Yield: 74 g (90.0% of theory; white powder).
Melting point: 72°–76°C.

EXAMPLE 4

410 g of $CF_3(CF_2)_nCH_2CHFI$ (wherein $n = 5, 7, 9, 11$), 30 g of ethylene and 10 g of catalyst according to Example 1 are reacted as described in Example 1.
Reaction conditions: 15 hours at 160°C; 75 kp/cm².
Reaction product:

| Composition according to gas chromatography: | | Mass spectrum |
|---|---|---|
| 18.45 % of | $C_6F_{13}CH_2CHFCH_2CH_2I$ | M 520 |
| 36.85 % of | $C_8F_{17}CH_2CHFCH_2CH_2I$ | M 620 |
| 17.00 % of | $C_{10}F_{21}CH_2CHFCH_2CH_2I$ | M 720 |
| 2.80 % of | $C_{12}F_{25}CH_2CHFCH_2CH_2I$ | M 820 |

The remainder to 100% is starting material which can be used in a further reaction.

Yield: 322.5 g (75.0% of theory) of a waxy, white powder.

EXAMPLE 5

100 g of $CF_3(CF_2)_nCH_2CHFI$ (wherein $n = 5, 7, 9$), 25 g of propene, and 1 g of catalyst according to Example 1 are reacted as described in Example 1.
Reaction conditions: 24 hours at 150°C; 30 kp/cm².
Reaction product: Composition according to gas chromatography and mass spectrum:

| | | |
|---|---|---|
| 20.55 % of | $C_6F_{13}CH_2CHFCH_2CH(CH_3)I$ | M 534 |
| 25.68 % of | $C_8F_{17}CH_2CHFCH_2CH(CH_3)I$ | M 634 |
| 6.30 % of | $C_{10}F_{21}CH_2CHFCH_2CH(CH_3)I$ | M 734 |

The remainder to 100% is starting material which can be used in a further reaction.
Yield of product: 54.10 g of yellow wax.

EXAMPLE 6

100 g of $CF_3(CF_2)_n(CH_2CF_2)_pI$ (wherein $n = 5, 7, 9$; $p = 1, 2$), 20 g of propene, and 2 g of catalyst according to Example 1 are reacted as described in Example 1.
Reaction conditions: 20 hours at 150°C; 30 kp/cm².
Reaction product: Composition according to gas chromatography and mass spectrum:

| | | |
|---|---|---|
| 1.36% of | $C_6F_{13}CH_2CF_2CH_2CH(CH_3)I$ | M = 552, M − I = 425 |
| 34.95% of | $C_8F_{17}CH_2CF_2CH_2CH(CH_3)I$ | M = 652, M − I = 525 |
| 23.16% of | $C_{10}F_{21}CH_2CF_2CH_2CH(CH_3)I$ | M = 752, M − I = 625 |
| 3.49% of | $C_6F_{13}(CH_2CF_2)_2CH_2CH(CH_3)I$ | M = 616, M − I = 489 |
| 8.76% of | $C_8F_{17}(CH_2CF_2)_2CH_2CH(CH_3)I$ | M = 716, M − I = 589 |
| 2.64% of | $C_{10}F_{21}(CH_2CF_2)_2CH_2CH(CH_3)I$ | M = 816, M − I = 689 |

The remainder to 100% is starting material which can be used in a further reaction.
Yield: 70.0 g of a pale yellow wax.

EXAMPLE 7

41 g of $C_4F_9CH_2CF_2I$, 11 g of allyl alcohol, and 1.2 g of a catalyst consisting of 0.1 g of CuCl, 0.1 g of SnCl₄, 0.4 g of diethanolamine, 0.6 g of Al₂O₃, are reacted as described in Example 1.
Reaction conditions: 5 hours at 140°C and normal pressure.
Yield: 13.0 g (28% of theory).
Boiling point: 103°–105°C/3 Torr.
Mass spectrum:
M = 468
M − OH = 451
M − CF₃ = 397
M − I = 341
Molecular weight of the compound of the formula

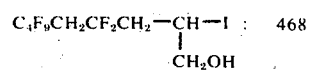

468

What we claim is:
1. Polyfluoroalkyl iodides of the formula

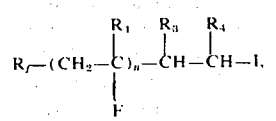

wherein $R_f$ represents fluorinated alkyl of 3 to 18 carbon atoms, $R_1$ represents hydrogen or fluorine, $R_3$ and $R_4$ each independently represents hydrogen, alkyl with 1 to 4 carbon atoms and $n$ is a whole number from 1 to 3.

2. Polyfluoroalkyl iodides according to claim 1, of the formula

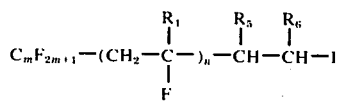

wherein $R_1$ represents hydrogen or fluorine, $R_5$ and $R_6$ each independently represents hydrogen, methyl and ethyl, $m$ is a whole number from 4 to 12 and $n$ is a whole number from 1 to 3.

3. Polyfluoroalkyl iodides according to claim 1, of the formula

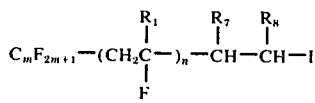

wherein $R_1$ represents hydrogen or fluorine, $R_7$ represents hydrogen, $R_8$ represents hydrogen, methyl and ethyl, $m$ is a whole number from 4 to 12 and $n$ is a whole number from 1 to 3.

4. Polyfluoroalkyl iodides according to claim 3, of the formula

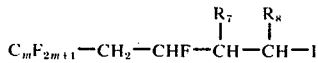

wherein $R_7$, $R_8$ and $m$ have the meanings given in claim 3.

5. Polyfluoroalkyl iodides according to claim 3, of the formula

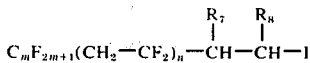

wherein $R_7$, $R_8$, $m$ and $n$ have the meanings given in claim 3.

6. Polyfluoroalkyl iodides according to claim 3, of the formula

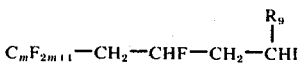

wherein $R_9$ represents hydrogen, methyl, and $m$ is a whole number from 4 to 12.

7. Polyfluoroalkyl iodides according to claim 3, of the formula

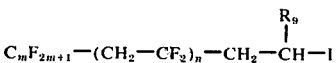

wherein $R_9$ represents hydrogen, methyl, $n$ is a whole number from 1 to 3 and $m$ is a whole number from 4 to 12.

8. Perfluoroalkyl iodides of claim 1 of the formula

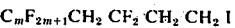

wherein $m$ is an integer of 4 to 12.

* * * * *